United States Patent [19]

Arlt et al.

[11] 4,419,297

[45] Dec. 6, 1983

[54] PREPARATION OF NITRILES FROM FORMAMIDES

[75] Inventors: Dieter Arlt, Cologne; Gerhard Klein, Monheim, both of Fed. Rep. of Germany

[73] Assignee: Bayer Aktiengesellschaft, Leverkusen, Fed. Rep. of Germany

[21] Appl. No.: 340,902

[22] Filed: Jan. 20, 1982

[30] Foreign Application Priority Data

Feb. 14, 1981 [DE] Fed. Rep. of Germany ....... 3105452

[51] Int. Cl.³ .................. C07C 120/00; C07C 120/10
[52] U.S. Cl. ............................... 260/465.2; 260/464; 260/465 B
[58] Field of Search .................. 260/465.2, 465 B, 464

[56] References Cited

U.S. PATENT DOCUMENTS

| | | | |
|---|---|---|---|
| 2,121,551 | 6/1938 | Rigby | 260/465.2 |
| 2,417,749 | 3/1947 | Hagemeyer, Jr. | 260/465.2 |
| 2,458,373 | 1/1949 | Hagemeyer, Jr. | 260/465.2 |
| 3,256,311 | 6/1966 | Becke et al. | 260/464 |
| 3,514,478 | 5/1970 | Becke et al. | 260/465 B |
| 4,203,917 | 5/1980 | Delmon et al. | 260/465.2 X |
| 4,315,869 | 2/1982 | Merger et al. | 260/465.2 |

FOREIGN PATENT DOCUMENTS

| | | |
|---|---|---|
| 20950 | 5/1980 | European Pat. Off. . |
| 1068241 | 11/1959 | Fed. Rep. of Germany . |
| 2706863 | 9/1977 | Fed. Rep. of Germany . |

OTHER PUBLICATIONS

Chemical Abstracts, vol. 72, Jan. 5, 1970, pp. 348, 349,[3701b] (Grrenhalgh et al.).

*Primary Examiner*—Joseph Paul Brust
*Attorney, Agent, or Firm*—Sprung, Horn, Kramer & Woods

[57] ABSTRACT

Aliphatic, araliphatic or aromatic nitriles of the formula R—CN are obtained by reacting N-substituted formamides of the formula R—NHCHO with at least the stoichiometric quantity of an acylating agent (generally a carboxylic acid anhydride, such as acetic anhydride, or ketene) in the gas phase at temperatures above 250° C., without using a catalyst. The process is especially useful in the preparation of nitriles wherein the connecting carbon of R is a tertiary carbon atom. The nitriles are important intermediate products, for example for the preparation of herbicides, surface-active agents and anti-corrosive agents.

8 Claims, No Drawings

PREPARATION OF NITRILES FROM FORMAMIDES

The invention relates to an unobvious, non-catalytic process for the preparation of certain known carboxylic acid nitriles by dehydration and isomerization from formamides.

It is known to react N-substituted formamides over special catalysts at high temperatures, to give nitriles and water (see, for example, DE-OS (German Published Specification) Nos. 1,908,967, 2,036,503, 2,706,863 and 2,827,058).

In many cases, it is necessary to carry out the reaction at a low conversion, in order to achieve a satisfactory yield. This procedure requires recycling of the feed product and gives only a low space-time yield. A further considerable disadvantage of these known catalytic processes is that a number of formamides generally gives only very unsatisfactory yields of the desired nitrile and that the activity of the catalyst decays after a short time. In such cases, this known procedure is not industrially feasible. In particular, the yields, and the lives of the catalysts described, are not adequate for an industrial manufacturing process, if formamides of the formula R-NHCHO are employed, the radical R of which is an alkyl radical bonded to the nitrogen atom via a tertiary carbon atom (compare, for example, the selectivity figure in Example 3 of DE-OS (German Published Specification) No. 2,706,863). At relatively high temperatures, formamides of this type tend not only to undergo a decarbonylation, like formamides in general, but also an elimination of the radical R with the formation of an olefin.

According to the present invention we provide a process for the production of a nitrile of the general formula

R—CN  (I)

in which R represents a saturated or unsaturated aliphatic hydrocarbon radical having up to 17 carbon atoms (any carbon atoms of a multiple bond, which may be present, not being bonded directly to the nitrile group) or represents an araliphatic or aromatic hydrocarbon radical having in each case up to 12 carbon atoms, in which an N-substituted formamide of the general formula

R—NH—CHO  (II)

in which R has the abovementioned meaning (with any carbon atoms of a multiple bond, when R is an unsaturated hydrocarbon radical, not being bonded directly to the formamide group), is reacted with an at least stoichiometric quantity of an acylating agent in the gas phase at a temperature above 250° C., without using a catalyst.

The process of the present invention surprisingly allows compounds of formula (I) to be produced in a simple manner with good yields and with good selectivity.

The process according to the invention dispenses with the use of catalysts and thus avoids the drawbacks, caused by a short life and limited conversion, of the previously known catalytic processes. In particular, however, the process according to the invention enables even those nitriles to be prepared with high selectivity from the corresponding formamides, the nitrile group of which is bonded to tertiary carbon atoms.

The selectivities and yields achieved by the process according to the invention are particularly surprising, since it is known (compare J. Org. Chem. 33 (1968), pages 4050-4054) that the pyrolysis of N-formylacetamides gives nitriles in only very poor yields. N-formylcarboxylic acid amides are detectable also in the reaction mixture of the process according to the invention.

If, for example, N-tert.-butylformamide is used as the starting material and, for example, acetic anhydride is used as the acylating agent, the course of the reaction according to the present invention is illustrated by the following equation:

(CH$_3$)$_3$C—NH—CHO + (CH$_3$CO)$_2$O → (CH$_3$)$_3$C—CN + 2CH$_3$COOH

Preferred N-substituted formamides of formula (II) to be used as the starting materials are those in which R represents an aliphatic hydrocarbon radical having 3 to 16 carbon atoms and, particularly preferably, those hydrocarbon radicals which contain a tertiary carbon atom. Amongst the last-mentioned group, those hydrocarbon radicals are particularly preferred, the tertiary carbon atom of which is bonded directly to the formamide group.

The following may be mentioned as starting materials of the formula (II):

methyl-, ethyl-, n- and i-propyl, n-, i-, sec.- and tert.-butyl-formamide, 1,1-dimethylpropyl-formamide, 1,1-dimethylpropargyl-formamide, 1-methyl-pentyl-formamide, n-hexyl- and cyclohexyl-formamide, and isooctyl-, isononyl-, isododecyl-, isopentadecyl- and isohexadecyl-formamide. In particular, those formamides can advantageously be used which are readily available industrially by the so-called Graf-Ritter reaction from hydrogen cyanide and olefins; these include, for example, tert.-butylformamide which can be prepared from i-butene, and the abovementioned formamides having branched hydrocarbon radicals which can be prepared from oligomers of propene or i-butene (see, for example, German Patent Specification No. 870,856; Methodicum Chimicum, volume 6 (1974), page 710; Org. Reactions volume 17 (1969), pages 213 et seq.). N-tert.-butylformamide is a particularly preferred starting material of the formula (II).

According to the present invention, carboxylic acid anhydrides and/or ketene are generally used as the acylating agent. Preferably, acetic anhydride, ketene, or the anhydrides of the acids, the nitrile of which is to be produced (for example pivalic acid anhydride, if pivalonitrile is to be prepared) are used. As already indicated, the acylating agent is used in an at least stoichiometric quantity relative to the quantity of formamide employed, but preferably an excess in a molar ratio of 1.5 to 3:1 is employed. In addition to the desired nitrile, the carboxylic acid on which the acylating agent is based is formed as a reaction product and, if the process is carried out industrially, this carboxylic acid can be reconverted again to the acylating agent which is to be employed according to the process.

To obtain a good selectivity, it is important to avoid a liquid-phase reaction. In general, the reaction is carried out in such a way that the reactants are vaporized, together or separately, and are introduced into a reaction zone, the reaction mixture being heated to the requisite temperature. The necessary temperature can be provided, for example, by external heating, but it is also possible to heat the acylating agent upstream of the reaction zone and to utilize it as a heat carrier.

The reaction can be carried out with or without dilution with an inert gas. In general, it is carried out in a temperature range between 320° and 500° C. It can be advantageous to control the reaction by accurate regulation of the temperature. Thus, a very good selectivity to a nitrile of formula (I) is achieved by first reacting the N-substituted formamide of formula (II) at a temperature of between 390° and 420° C. to give an acylated formamide which is then broken down in a higher temperature range from 420° to 500° C. in the desired manner to give a nitrile of formula (I) and a carboxylic acid.

The vaporization and reaction of the starting components can be carried out either under normal pressure or under reduced pressure. Conventional, industrially utilized vaporizers can be used, for example coiled tube vaporizers and falling film vaporizers. The reaction is carried out, for example, in VA stainless steel reaction tubes. The process can also be carried out in a fluid or fluidized bed. After they have left the reaction zone, the reaction products are cooled and condensed. The mixture of substances is in general separated by a fractional vacuum distillation. During working-up, prolonged heating of the liquid phase to temperatures above 100° C. must be precluded in order to avoid a reduction in yield.

The nitriles of formula (I) which can be prepared by the process according to the invention are valuable intermediate products, for example for the preparation of herbicides, surface-active agents and anti-corrosive agents.

Thus, for example, pivalonitrile (the compound of formula (A)) can be converted by catalytic hydrogenation into neopentylamine (the compound of formula (B)) which can be reacted by various routes to give the known herbicidally active compound 1-amino-6-ethylthio-3-neopentyl-1,3,5-triazine-2,4(1H,3H)-dione (the compound of formula (K)) as indicated below (see example, Danish Patent Specification No. 136,067);

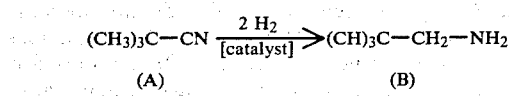

One process route proceeds via the following stages (see Belgian Patent Specification No. 682,820; Angew. Chem. 82 (1970), pages 63–67; Synthesis 1970, pages 542–543; DE-OS (German Published Specification) No. 2,254,200):

(B) ⟶ (CH₃)₃C—CH₂—NH—CHO +
(C)

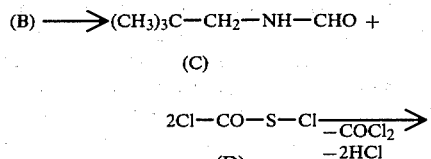

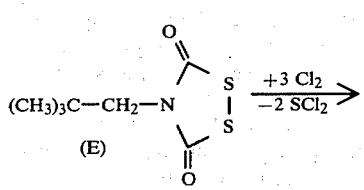

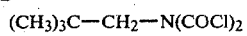

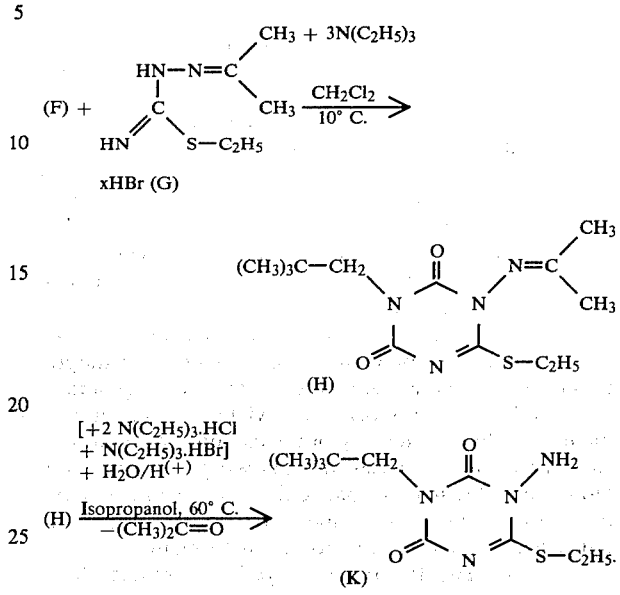

Another process route proceeds via the following stages (see DE-OS (German Published Specification) No. 3,006,226 and DE-OS (German Published Specification) No. 3,006,263):

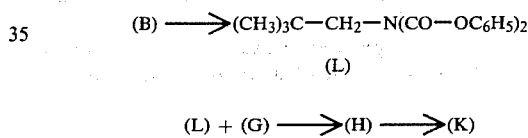

(L) + (G) ⟶ (H) ⟶ (K)

The preparative examples which follow illustrate the process according to the present invention in more detail.

PREPARATIVE EXAMPLES

EXAMPLE 1

Preparation of pivalonitrile, (CH₃)₃C—CN.

Per hour, 23 g of N-tert.-butylformamide and 69 g of acetic anhydride were metered separately into a prevaporizer, heated in each case to 220° C., and the gases were metered into a quartz tube (cross-section of the tube 90 mm, volume 1,180 ml) which was filled with Raschig rings (diameter 12 mm) and was electrically heated to 420° C. The pyrolysis gases were condensed in a cooled receiver; 91.7 g of condensate were obtained per hour. The selectivity, determined by gas chromatography, was 92%, relative to pivalonitrile, at a conversion of 88%.

EXAMPLE 2

Preparation of pivalonitrile, (CH₃)₃C—CN.

Per hour, 69 g of a mixture of pivalic acid anhydride and N-tert.-butylformamide (weight ratio 2.8:1) were introduced dropwise into a V4A stainless steel tube (cross-section 8 mm, volume 800 ml) heated to 420° C. With a residence time of 111 seconds, the resulting selectivity, determined by gas chromatography, was 93%, relative to pivalonitrile, at a conversion of 94%. The running time was 122 hours.

EXAMPLE 3

(a) Preparation of N-(1,1-dimethyl-propyl)-formamide,

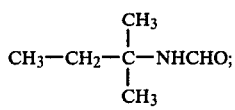

by a Graf-Ritter reaction:

210 g of 2-methyl-but-2-ene and 54 g of water were simultaneously added dropwise, in the course of one hour, to a solution of 250 ml of hydrocyanic acid in 410 g of methanesulphonic acid; during the addition, the reaction temperature was maintained at 20° to 40° C. by cooling. After 4 hours, excess hydrocyanic acid was distilled off, the residue was neutralized with ice/sodium hydroxide solution and the formamide was then extracted with methylene chloride. The solution in methylene chloride was worked up by distillation. 245 g of N-(1,1-dimethyl-propyl)-formamide were obtained.

(b) Preparation of 2-methyl-butyro-2-nitrile,

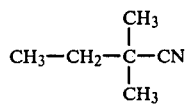

115 g of N-(1,1-dimethyl-propyl)-formamide and 300 g of acetic anhydride were metered in the course of 5 hours into an apparatus as described in Example 1, the temperature in the pre-vaporizer being 240° C. and the average temperature in the tube reactor being 430° C. 402 g of a pyrolysis product were obtained which, according to analysis by gas chromatography, contained 19.5% (80% selectivity) of 2-methyl-butyro-2-nitrile.

The product was isolated by fractional distillation (boiling point 130°-131° C.).

EXAMPLE 4

Preparation of pivalonitrile, $(CH_3)_3C$—CN.

Per hour, 60 g of a mixture of acetic anhydride and N-tert.-butylformamide (weight ratio 3:1) were introduced dropwise into a V4A stainless steel tube (internal diameter 8 mm, volume 750 ml) electrically heated to 400° C. The residence time was 83 seconds. The pyrolysis product was largely condensed in a product cooler and a receiver vessel which was cooled with cooling brine at −20° C. After 147 hours, the experiment was terminated. 8,670 g of a condensate were obtained, for which an analysis by gas chromatography gave a selectivity to pivalonitrile of 84%, at a conversion of 83%. The condensate could be worked up by distillation under 300 mbars, without any side reactions of the unconverted N-tert.-butylformamide.

EXAMPLE 5

Preparation of pivalonitrile, $(CH_3)_3C$—CN.

Per hour, 10 g of N-tert.-butylformamide and 19 g of ketene were metered into a V4A stainless steel tube (internal diameter 6 mm, volume 90 ml) electrically heated to 400° C. The residence time was 40 seconds. The pyrolysis product was condensed in a receiver vessel cooled to −20° C. This gave 22.0 g of a condensate which, according to analysis by gas chromatography, contained 24.9% of pivalonitrile (selectivity 76%, conversion 87%).

EXAMPLE 6

Per hour, 44 g of N-tert.-butylformamide and 108 g of acetic anhydride were separately introduced dropwise into a pre-vaporizer, heated in each case to 220° C., and the gases were passed into a quartz tube (cross-section of the tube 90 mm, length 300 mm) which was filled with Raschig rings (diameter 12 mm).

The lower third of the reaction tube was heated to 450° C., and the upper part was heated to 420° C. The pyrolysis gases were condensed in a cooled receiver. 151 g of condensate were obtained per hour.

According to analysis by gas chromatography, the condensate contained 27.8 g of pivalonitrile and 7.9 g of unconverted N-tert.-butylformamide (selectivity of 94%, at a conversion of 82%). The running time was 500 hours.

It will be appreciated that the instant specification and examples are set forth by way of illustration and not limitation, and that various modifications and changes may be made without departing from the spirit and scope of the present invention.

We claim:

1. A process for the production of a nitrile of the formula

R—CN in which R is an aliphatic hydrocarbon radical having up to 17 carbon atoms, any carbon atoms or a multiple which may be present, not being bonded directly to the nitrile group or is an araliphatic or aromatic hydrocarbon radical in each case having up to 12 carbon atoms, comprising reacting an N-substituted formamide of the formula

R—NH—CHO with at least the stoichiometric quantity of an acylating agent in gas phase at a temperature from about 250° C. to 500° C. in the absence of a catalyst, the acylating agent being selected from the group consisting of acetic anhydride, ketene and the anhydride of the acid corresponding to the desired nitrile.

2. A process according to claim 1, wherein the reaction temperature is from about 320° to 500° C.

3. A process according to claim 1, wherein about 1.5 to 3 mols of the acylating agent are employed per mol of N-substituted formamide.

4. A process according to claim 1, wherein the acylating agent is acetic anhydride or ketene.

5. A process according to claim 1, wherein the acylating agent is the anhydride of the acid corresponding to the desired nitrile.

6. A process according to claim 1, wherein that carbon atom of R which is connected to —NH—CHO of the N-substituted formamide is a tertiary carbon atom.

7. A process according to claim 1, wherein the N-substituted formamide is N-tert.-butylformamide.

8. A process according to claim 1, wherein, the acylating agent is pivalic anhydride, acetic anhydride or ketene, about 1.5 to 3 mols of the acylating agent are employed per mol of N-substituted formamide, and the reaction temperature is from about 230° to 500° C.

* * * * *